US011400089B2

(12) United States Patent
Tang-Liu et al.

(10) Patent No.: US 11,400,089 B2
(45) Date of Patent: Aug. 2, 2022

(54) MULTIKINASE INHIBITORS AND USES IN REPRODUCTIVE AND DIGESTIVE TRACT FIBROSIS

(71) Applicants: AIVIVA BIOPHARMA, INC., Las Vegas, NV (US); Diane Dan-Shya Tang-Liu, Las Vegas, NV (US)

(72) Inventors: Diane Dan-Shya Tang-Liu, Las Vegas, NV (US); Tiffany Constance Liu, Las Vegas, NV (US); Gerald Woodrow DeVries, San Clemente, CA (US)

(73) Assignees: Diane Dan-Shya Tang-Liu, Las Vegas, NV (US); AIVIVA BIOPHARMA, INC., Las Vegas, NV (US)

( * ) Notice: Subject to any disclaimer, the term of this patent is extended or adjusted under 35 U.S.C. 154(b) by 201 days.

(21) Appl. No.: 16/638,618

(22) PCT Filed: Aug. 13, 2018

(86) PCT No.: PCT/US2018/046505
§ 371 (c)(1),
(2) Date: Feb. 12, 2020

(87) PCT Pub. No.: WO2019/036367
PCT Pub. Date: Feb. 21, 2019

(65) Prior Publication Data
US 2021/0369712 A1     Dec. 2, 2021

Related U.S. Application Data

(60) Provisional application No. 62/544,825, filed on Aug. 12, 2017.

(51) Int. Cl.
| | | |
|---|---|---|
| *A61K 31/5025* | (2006.01) | |
| *A61K 31/4439* | (2006.01) | |
| *A61K 31/47* | (2006.01) | |
| *A61K 31/506* | (2006.01) | |

(52) U.S. Cl.
CPC ...... *A61K 31/5025* (2013.01); *A61K 31/4439* (2013.01); *A61K 31/47* (2013.01); *A61K 31/506* (2013.01)

(58) Field of Classification Search
CPC .............. A61K 31/5025; A61K 31/506; A61K 31/4439; A61K 31/47
See application file for complete search history.

(56) References Cited

FOREIGN PATENT DOCUMENTS

CN     107019697 A     8/2017

OTHER PUBLICATIONS

Elshal, Naunyn-Schmiedeberg's Arch Pharmacol, vol. 388, 1293-1304, 2015. (Year: 2015).*
Delanote, BMC Pulmonary Medicine, VOl 16(156), 1-10, 2016. (Year: 2016).*
Huang, ACS Med Chem Lett, Sep. 2017, VOl 8(11), 1142-1147. (Year: 2017).*
Bulun, S.E., Uterine Fibroids, The New England Journal of Medicine, 369(14), 1344-1355, bearing an alleged date of Oct. 2013.
Everitt, J.I. et al., Rodent Model of Reproductive Tract Leiomyomata, Clinical and Pathological Features, American Journal of Pathology, 146(6), 1556-1567, bearing an alleged date of Jun. 1995.
Tal, R. et al., The role of angiogenic factors in fibroid pathogenesis: potential implications for future therapy, Human Reproduction Update, 20(2), 194-216, bearing an alleged date of Mar. 2014.
Kumar, A. et al., Primary Sclerosing Cholangitis: Therapeutic Options and Surveillance Management, Clinical Medicine Insights: Gastroenterology, 9, 25-29, bearing an alleged date of Sep. 2016.
Walsh, K. et al., Distribution of vascular endothelial growth factor (VEGF) in prostate disease, Prostate Cancer and Prostatic Diseases, 5(2), 119-122, bearing an alleged date of Jun. 2002.
Soulitzis, N. et al., Expression analysis of peptide growth factors VEGF, FGF2, TGFB1, EGF and IGF1 in prostate cancer and benign prostatic hyperplasia, International Journal of Oncology, 29(2), 305-314, bearing an alleged date of Aug. 2006.
Delanote, I. et al., Safety and efficacy of bridging to lung transplantation with antifibrotic drugs in idiopathic pulmonary fibrosis: a case series, BMC Pulmonary Medicine, 16(156), 1-10, bearing an alleged date of Nov. 2016.
Hilberg, F. et al., BIBF 1120: Triple Angiokinase Inhibitor with Sustained Receptor Blockade and Good Antitumor Efficacy, Cancer Research, 68(12), 4774-4782, bearing an alleged date of Jun. 2008.
International Search Report and Written Opinion, PCT/US2018/046505, dated Oct. 12, 2018.

* cited by examiner

*Primary Examiner* — D Margaret M Seaman
(74) *Attorney, Agent, or Firm* — Maschoff Brennan; Brent A. Johnson; David Old

(57) ABSTRACT

A method for preventing and/or treating fibrosis associated with a reproductive tract or digestive tract disease or disorder includes administering an effective amount of a multikinase inhibitor to an animal or human in need thereof. The multikinase inhibitor comprises axitinib, nintedanib, sunitinib, lenvatinib, regorafenib, ponatinib, pazopanib, riociguat, or a salt thereof. The reproductive tract or digestive tract disease or disorder comprises uterine fibroids or primary sclerosing cholangitis, including Intra uterine surgery, intra uterine synechiae, Asherman's syndrome, biliary duct fibrosis, biliary duct sclerosis, and primary biliary cirrhosis.

13 Claims, 14 Drawing Sheets

FIG. 1 Prostate weight / 100g body weight Study Termination.
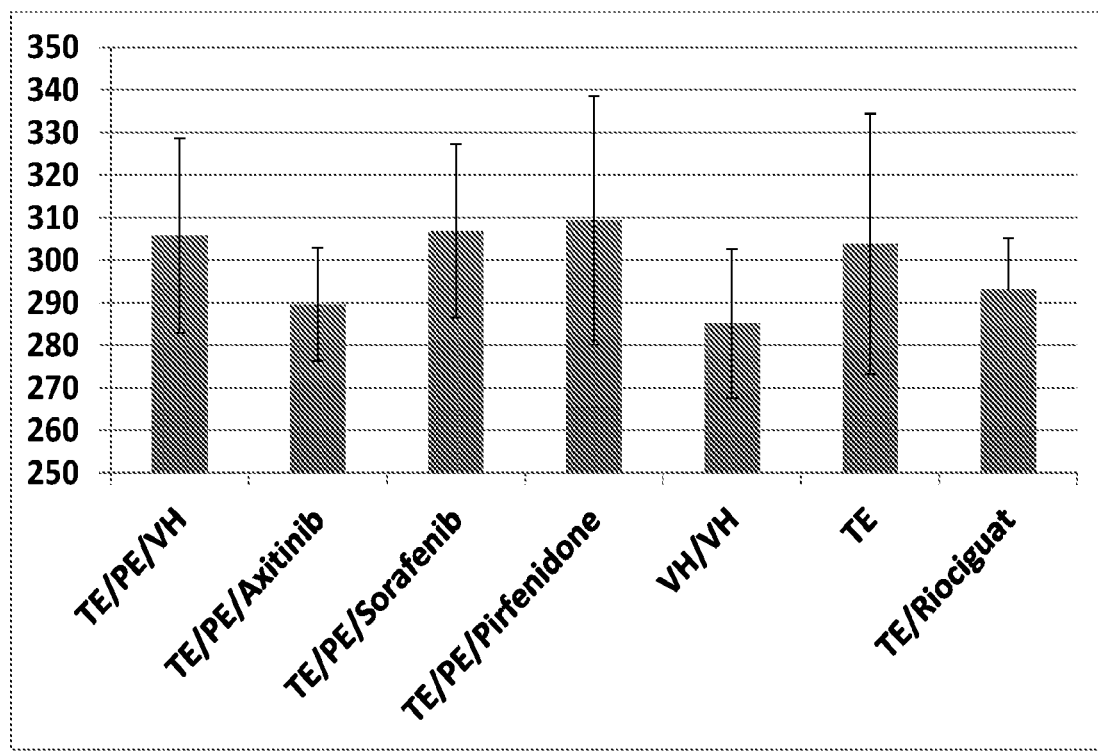
FIG. 2
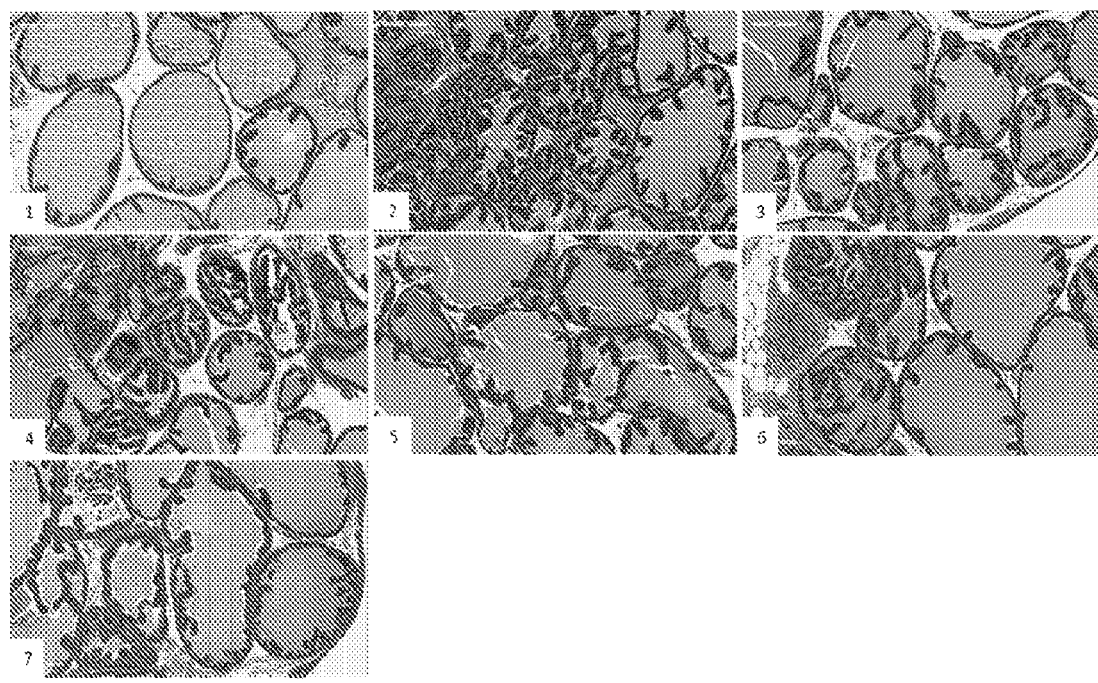

FIG. 3. Dorsolateral Prostate Hyperplasia Score

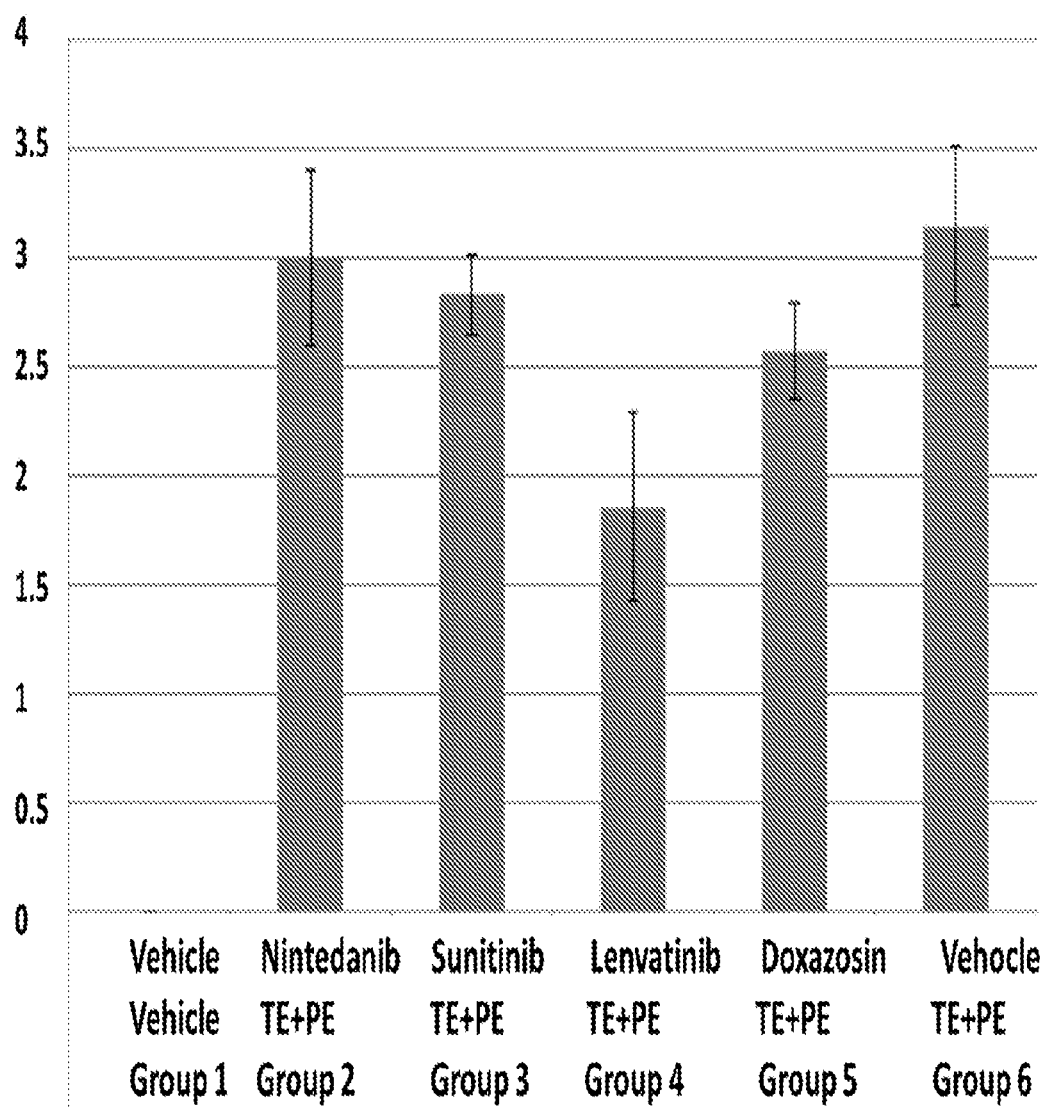
FIG. 6 Glandular Hyperplasia Mean Scores in the Dorsolateral Prostate

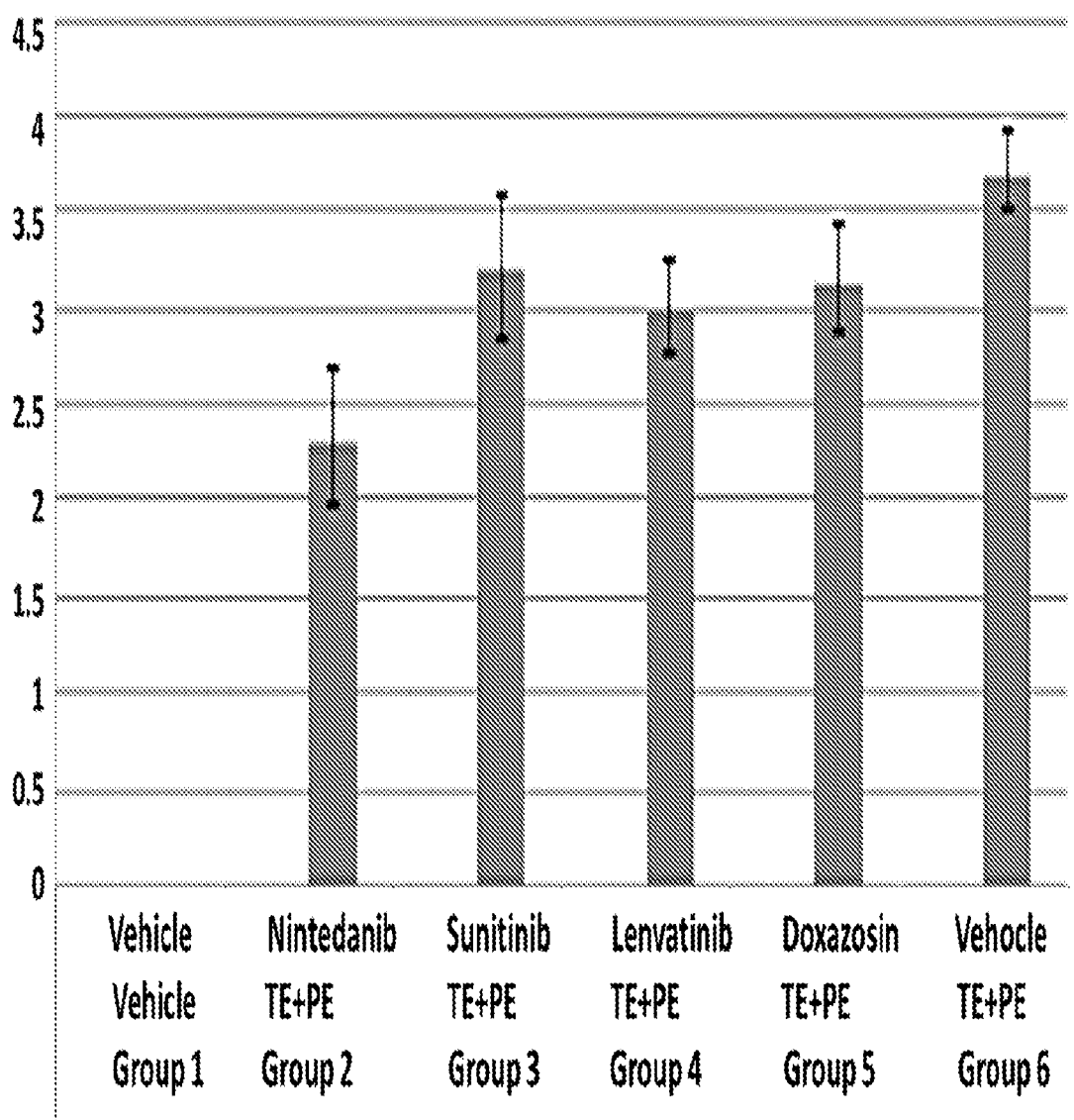
FIG. 7    Glandular Hyperplasia Mean Scores in the Ventral Prostate

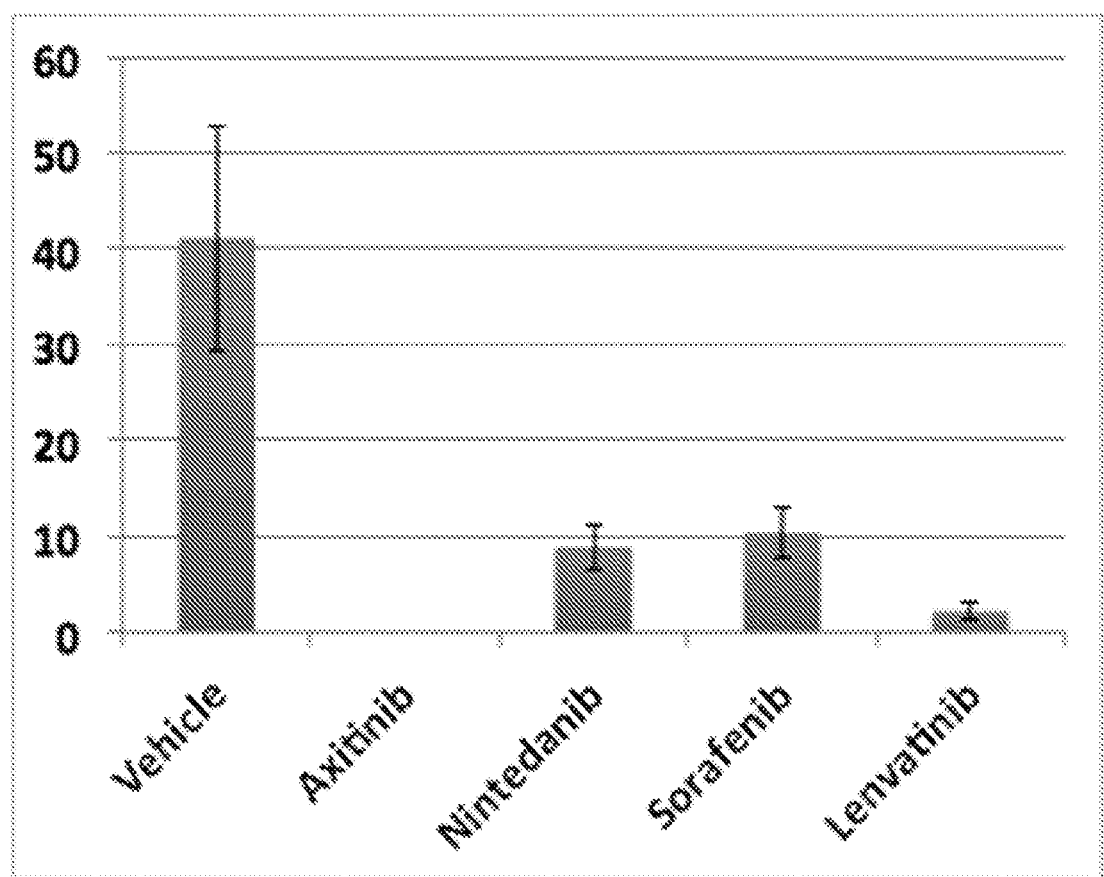
FIG. 8  Total Corneal Vessel Area (mm$^2$)

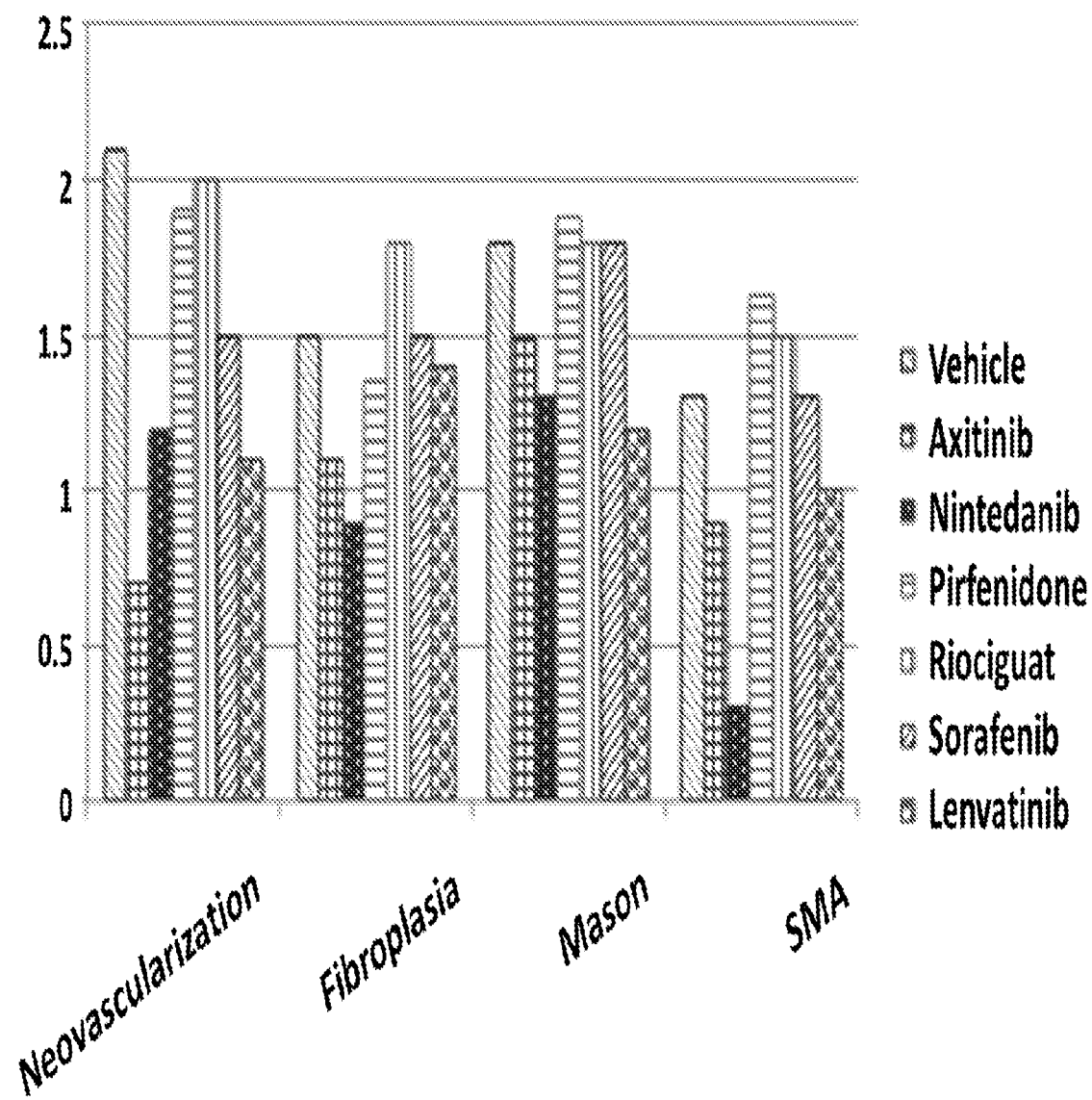
FIG. 9 Histological Findings Corneal Suture Fibrosis Model

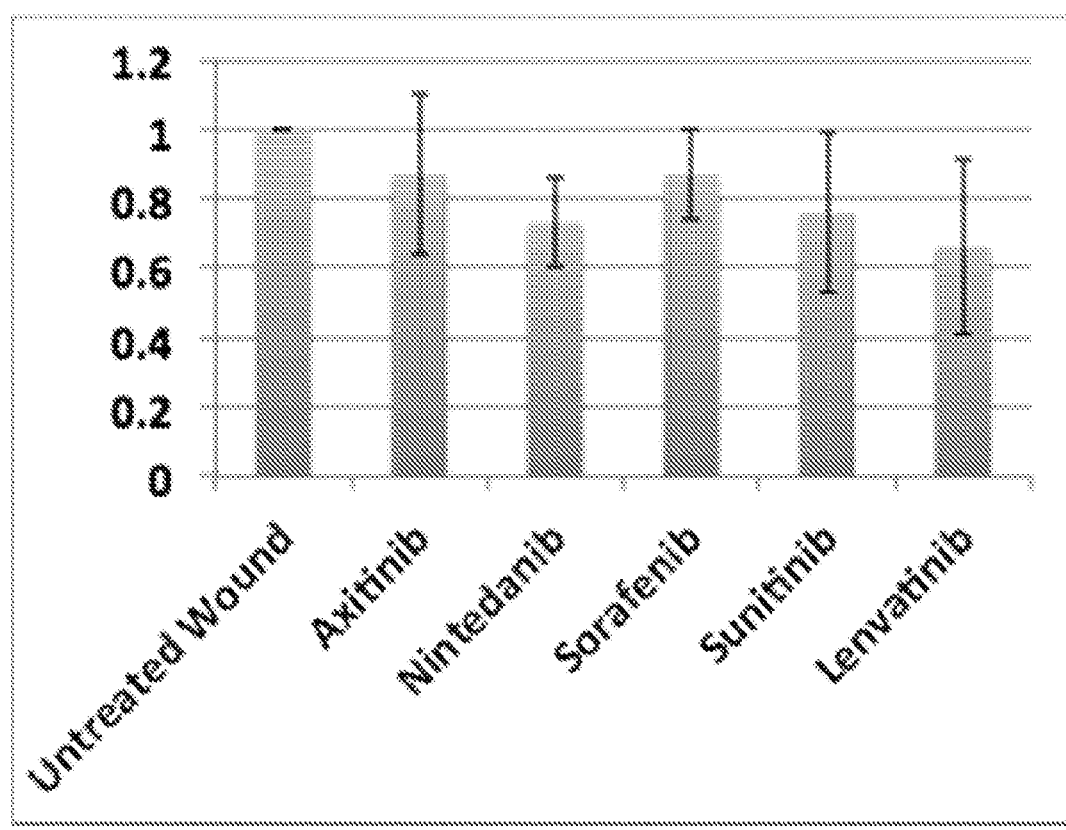
FIG. 10  TGF beta1 mRNA Expression in Rabbit Dermal Wound Model

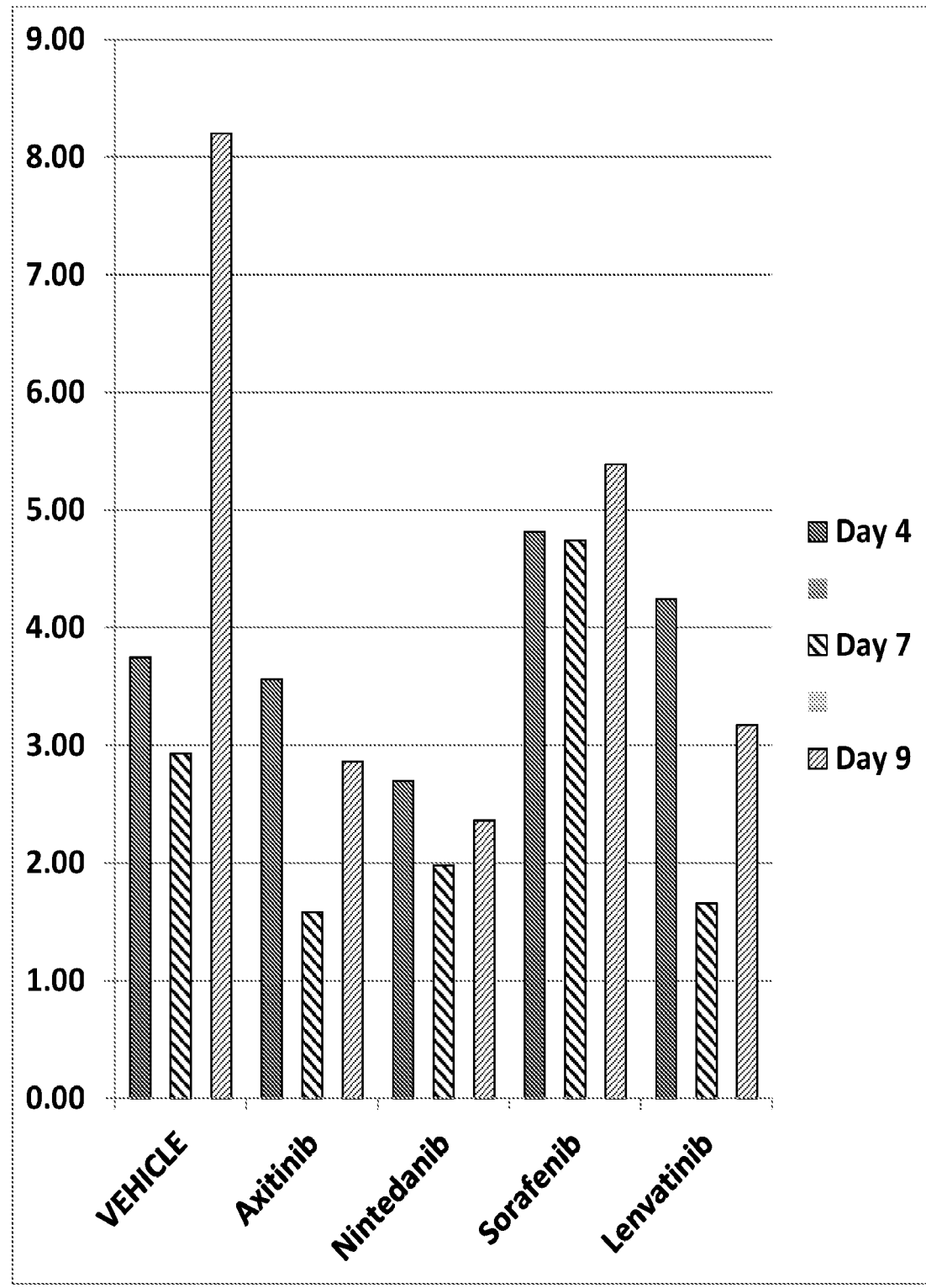
FIG. 11  Dermal TGF beta1 Levels (pg TGFB1 per ug total protein) in Pig Linear Incision Wound Model

FIG. 12 Percent TGFb1 mRNA Expression for Mice Treated with Water and Vehicle, Mice Induced with LL37 and Vehicle, and Mice Induced with LL37 and Treated with Lenvatinib.
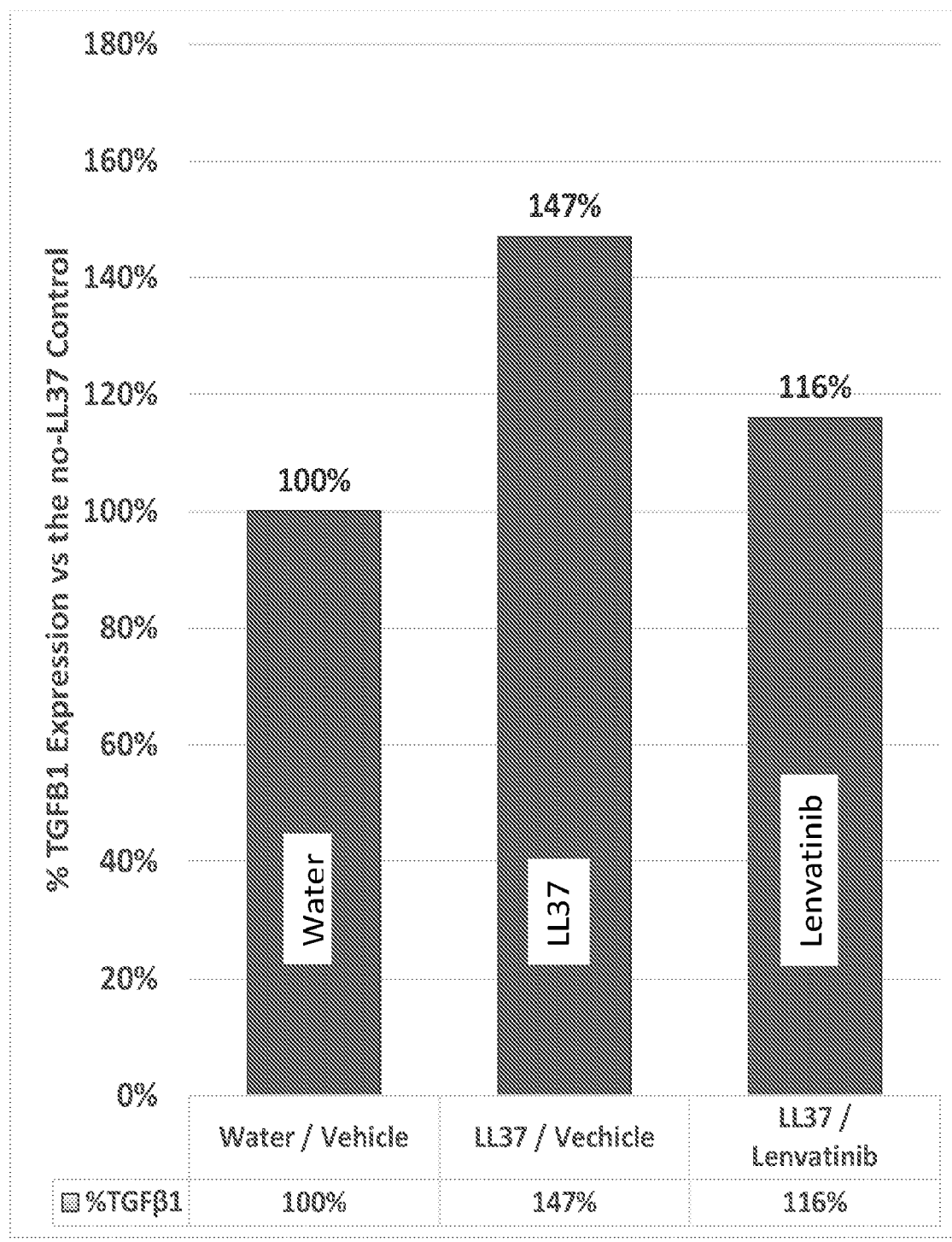

FIG. 13 Inflammation Scores of Treatment Groups with Intradermal LL37 Induction in Mice.
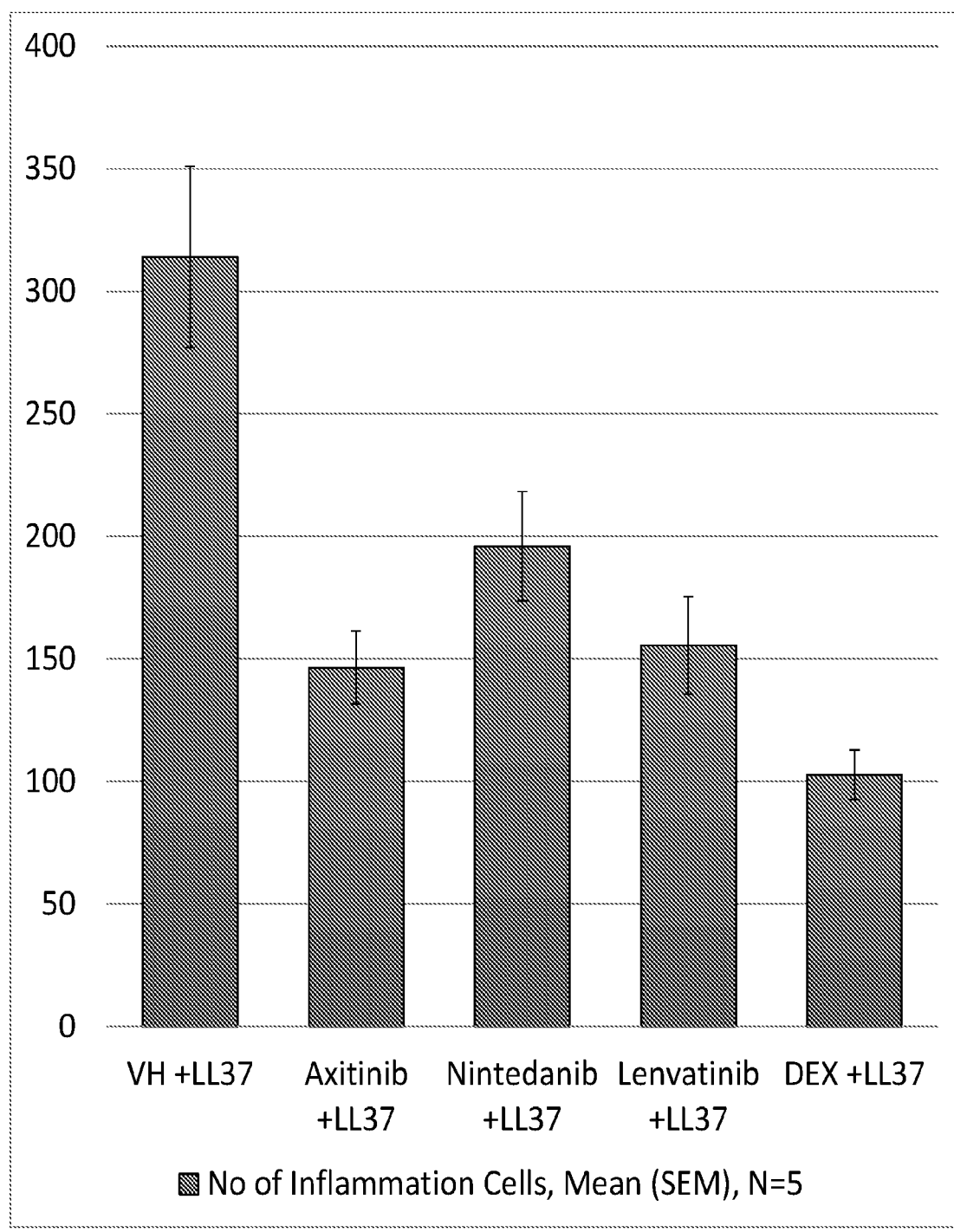

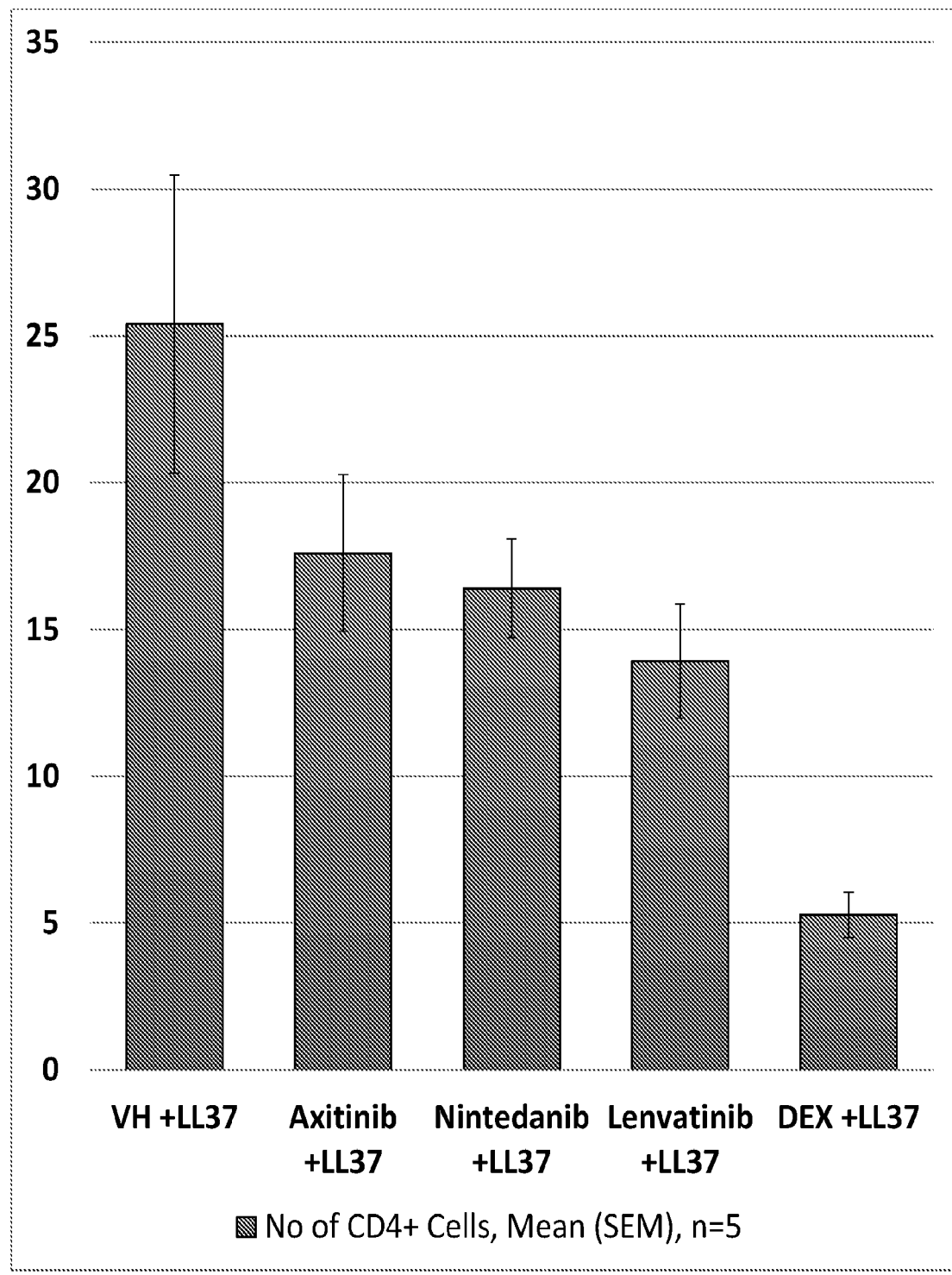
FIG. 14 CD4 Lymphocyte Scores of Treatment Groups with Intradermal LL37 Induction in Mice.

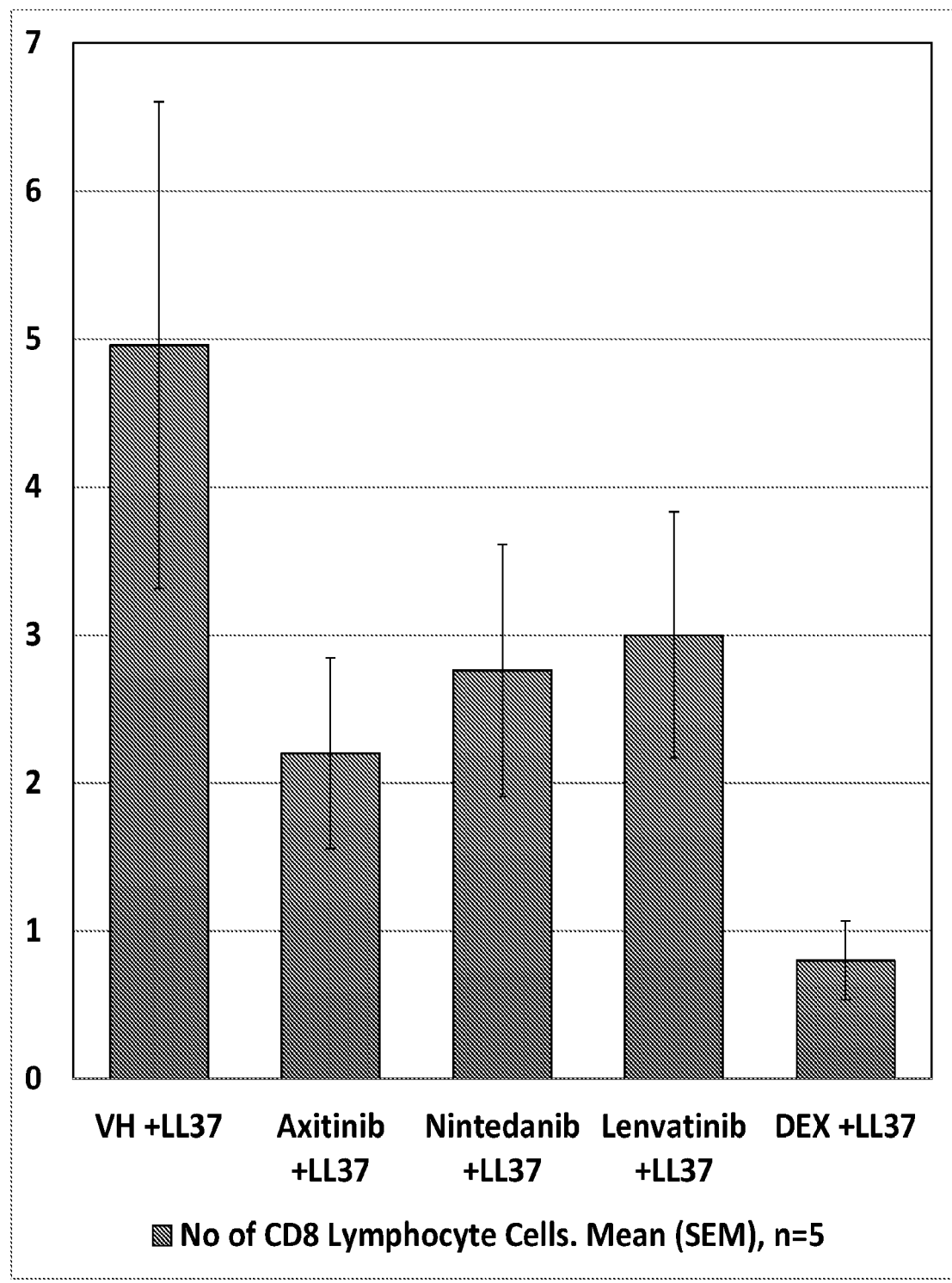
FIG. 15 CD8 Lymphocyte Scores of Treatment Groups with Intradermal LL37 Induction in Mice.

MULTIKINASE INHIBITORS AND USES IN REPRODUCTIVE AND DIGESTIVE TRACT FIBROSIS

CROSS-REFERENCE TO RELATED APPLICATIONS

This application is a national phase application of PCT/US2018/046505, filed on Aug. 13, 2018, which claims the benefit of U.S. Provisional Application No. 62/544,825, filed Aug. 12, 2017, which is incorporated by reference herein in its entirety.

FIELD

The disclosure relates to compounds that possess a certain spectrum of multikinase inhibition activities, which act on specific growth factors and/or cytokine signaling pathways and/or phases of fibrotic responses. The disclosure also relates to methods of prevention and/or treatment of disease states and/or disorders associated with fibrosis, such reproductive tract diseases and disorders, including uterine fibroids, and digestive tract diseases and disorders, including primary sclerosing cholangitis (PSC).

BACKGROUND

Fibrosis is involved in the pathogenesis, or failure of treatment, of a number of diseases and/or disorders affecting the reproductive and/or digestive tracts in humans. Fibrosis is the formation of excess extracellular matrix in an organ or tissue as the result of a reparative or reactive process. The complexity of these responses has resulted in significant challenges in developing anti-fibrotic therapeutics.

A significant fibrotic disease affecting the reproductive tract in women is uterine fibroids. Uterine fibroids (leiomyomas) are monoclonal tumors that arise from the myometrium. Myomas can be developed in the cervix. These fibroids are benign neoplasms composed of disordered smooth-muscle cells buried in abundant quantities of extracellular matrix. The exact causes of these fibroids are currently unknown. Their growth has been reported to be dependent on hormonal, genetic, and growth factors.

Leiomyomas are rare in animals and there is no universally-accepted experimental model. The Eker rat develops tumors that resemble fibroids, but the growths do not exhibit the abundant collagen characteristic of the human tissue. While murine models have been reported, they have not been widely adopted. Surgical specimens of the tumor or tumor-derived cells might not be in a state of active growth, or alternatively be in a state of senescence at the time of acquisition. Because of this complexity, the identification of key molecular pathways in tumor development remains elusive and presents challenges to pharmaceutical development.

Today the medical treatment options are limited, and often not helpful, for most patients with bleeding, pain, and growth of the fibroids continuing over a long term. Medical therapy may help to decrease the bleeding associated with fibroids over the short term. Types of medical therapy include hormones that block the effect of estrogen or progesterone, or reduce or eliminate the production of these hormones from the ovaries.

A number of growth factors have been identified as important agents in the development of extracellular matrix in uterine fibroids. PDGF, for example, has been reported to increase collagen 1 in both leiomyoma and myometrial cells. Furthermore, the TGF beta superfamily is known to be involved in the accumulation of extracellular matrix in leiomyomas. TGF beta increases collagen 1 mRNA expression in myometrial and leiomyoma cells, and increases fibronectin mRNA expression in these cells [Islam S et al., Ibid]. Inhibition of growth factor receptor signaling may have a significant impact on extracellular matrix formation in fibroids.

It has also been suggested that angiogenesis may play an important role in the regulation of leiomyoma growth. Multiple growth factors involved in angiogenesis are differentially expressed in leiomyoma, as compared with myometrium. These growth factors include VEGF, basic FGF, PDGF and TGF beta. Targeting angiogenic growth factors and growth factor receptors to block angiogenesis represents a novel therapeutic approach to uterine fibroid treatment.

Primary sclerosing cholangitis (PSC) is a chronic immune mediated liver disease characterized by inflammation and fibrosis of both intra- and extrahepatic bile ducts. This results in progressive fibrostenotic strictures of the entire biliary tree, eventually leading to liver cirrhosis, portal hypertension, and end-stage liver disease. Due to the complex nature of PSC, it seems to be very likely that no single perfect experimental PSC model will ever be generated. Attempts at medical treatment have proven problematic. Ursodeoxycholic acid (UDCA) has proven to be effective in primary biliary cirrhosis, but its use for PSC has been controversial. The use of immunosuppressive therapy in PSC has shown little impact with no evidence of long-term efficacy or delay in progression to end-stage disease. Tacrolimus, azathioprine, and corticosteroids have demonstrated modest improvements in liver biochemistry. However, these effects were not sustained and did not show clinical benefits. Currently, there are no recognized effective medical treatments for PSC. Liver transplantation is the only therapeutic modality that appears to change the prognosis for PSC. Clearly, there is a large unmet clinical need in this patient population.

There are no animal models for uterine fibrosis and/or PSC that are directly applicable to human uterine fibroids and primary sclerosing cholangitis. Studies based on examination of the underlying pathophysiology, such as benign tissue growth and fibrotic accumulation, however, can give important insights into the development of effective therapeutic strategies. Commonalities, such as the role of fibrosis and angiogenesis in both uterine fibroids and primary sclerosing cholangitis, point to a possibility that inhibition of growth factors and growth factor receptors will be useful in the treatment and/or prevention of these reproductive and digestive tract diseases. Specifically, compounds with a certain spectrum of inhibitory activities useful in this regard are identified in this disclosure.

SUMMARY

The present disclosure relates to agents which possess a certain spectrum of multikinase inhibitor activities and are accordingly useful in methods of treatment of disease states and/or disorders associated with reproductive tract or digestive tract fibrosis in animals and humans. More specifically, the disclosure is also directed to the therapeutic or prophylactic uses of such compounds and compositions, and to methods of treating disease states and/or disorders associated with reproductive tract or digestive tract fibrosis. These disorders may include, but not limited to, uterine fibroids, uterine fibroma, intramural fibroids, subserosal fibroids, submucosal fibroids, pedunculated fibroids, uterine leiomyomas, uterine myomas, adenomyosis, uterine fibromyoma, uterine fibroleiomyoma, cervical fibroids, uterine synechiae, Asherman's syndrome, biliary duct fibrosis, biliary duct sclerosis, primary biliary cirrhosis, and primary sclerosing cholangitis.

Some embodiments include a method for treating/preventing uterine fibroids or primary sclerosing cholangitis by administering a therapeutically effective amount of a multikinase inhibitor to a human subject in need of such treatment or prevention, wherein the multikinase inhibitor may include, but not limited to, axitinib, nintedanib, sunitinib, lenvatinib, regorafenib, ponatinib, pazopanib, and riociguat.

BRIEF DESCRIPTION OF DRAWINGS

FIG. 1 shows effects of test agents on testosterone and phenylephrine induced prostate weights in rats.

FIG. 2 shows effects of test agents on testosterone and phenylephrine induced fibroplasia in rats. Representative images from dorsolateral prostate at 100×magnification are shown.

FIG. 6 shows glandular hyperplasia mean scores in the dorsolateral prostate.

FIG. 7 shows glandular hyperplasia mean scores in the ventral prostate.

FIG. 8 shows total corneal vessel area ($mm^2$).

FIG. 9 shows histological findings in a corneal suture fibrosis model.

FIG. 10 shows TGF beta 1 mRNA expression in a rabbit dermal wound model.

FIG. 11 shows dermal TGF beta 1 level (pg TGFB1 per µg total protein) in a pig linear incision wound model FIG. 12 shows TGFb1 mRNA Expression for Mice Treated with Water and Vehicle, Mice Induced with LL37 and Vehicle, and Mice Induced with LL37 and Treated with Lenvatinib.

FIG. 13 shows inflammation Scores of Treatment Groups with Intradermal LL37 Induction in mice.

FIG. 14 shows CD4+ Lymphocyte Scores after treatments with some of the multi-kinase inhibitors described herein in intradermal LL37 injection-induced inflammation model in mice.

FIG. 15 shows CD8+ Lymphocyte Scores after treatments with some of the multi-kinase inhibitors described herein in intradermal LL37 injection-induced inflammation model in mice.

DETAILED DESCRIPTION

Figure 3:
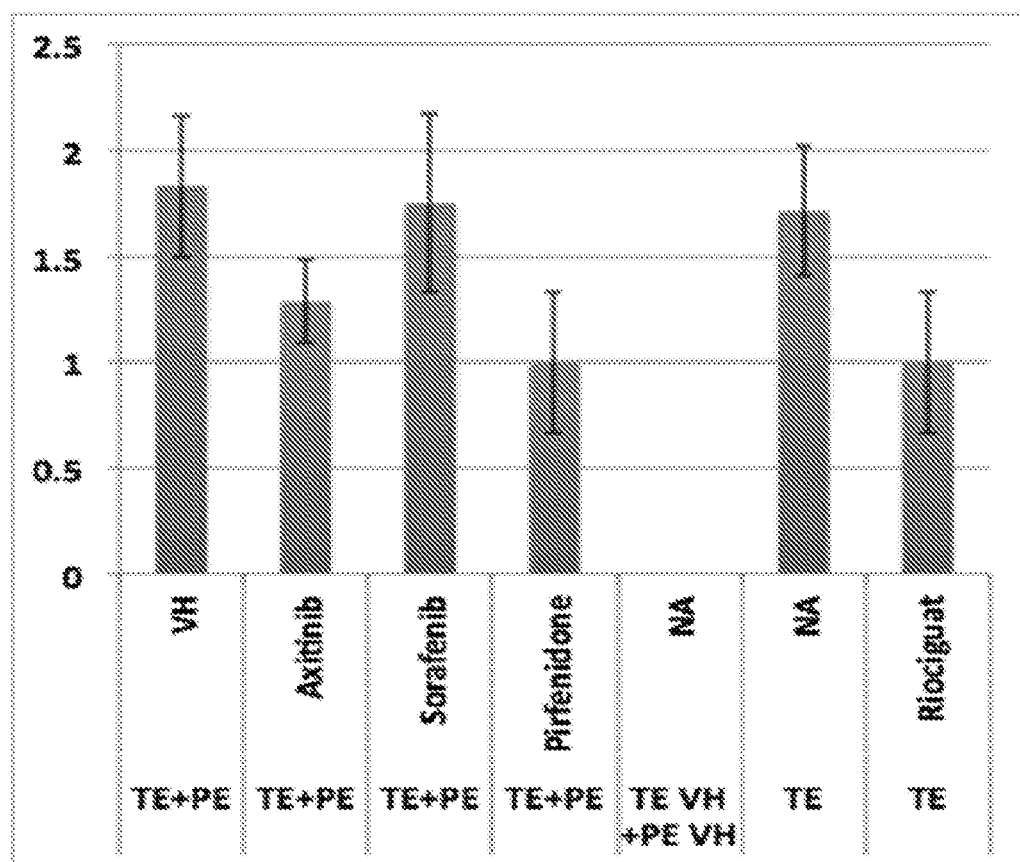
FIG. 3 shows mean dorsolateral prostate hyperplasia Scores.

Embodiments of the present disclosure relate to multikinase inhibitors that possess a certain spectrum of kinase inhibition activities. These inhibitors, being able to inhibit multiple kinases, are referred to as "multikinase inhibitors" in this description. Multikinase inhibitors described herein are useful in the treatment and/or prevention of fibrosis associated with disease states and/or disorders of reproductive tract or digestive tract in animals or humans. These disorders may include, but not limited to, uterine fibroids, uterine fibroma, intramural fibroids, subserosal fibroids, submucosal fibroids, pedunculated fibroids, uterine leiomyomas, uterine myomas, adenomyosis, uterine fibromyoma, uterine fibroleiomyoma, biliary duct fibrosis biliary duct sclerosis, primary biliary cirrhosis, and primary sclerosing cholangitis.

Of particular interest are axitinib, nintedanib, sunitinib, lenvatinib, regorafenib, ponatinib, pazopanib, riociguat, or a combination thereof, for the treatment of uterine fibroids, uterine fibroma, intramural fibroids, subserosal fibroids, submucosal fibroids, pedunculated fibroids, uterine leiomyomas, uterine myomas, adenomyosis, uterine fibromyoma, uterine fibroleiomyoma, biliary duct fibrosis, biliary duct sclerosis, primary biliary cirrhosis, and primary sclerosing cholangitis.

In some embodiments, a multikinase inhibitor such as nintedanib (or another compound with similar activity) is used to treat uterine myomas (such as uterine parasitic myomas), adenomyosis, uterine fibromyoma, uterine fibroleiomyoma, intra uterine surgery, Asherman's syndrome, intrauterine adhesions and intrauterine synachiae.

The term "treating" or "treatment" broadly includes any kind of treatment activity, including the diagnosis, cure, mitigation, or prevention of disease in human beings or other animals, or any activity that otherwise affects the structure or any function of the body of human beings or other animals.

A multikinase inhibitor may be administered by any suitable route, such as a parenteral route, e.g. by injection. For example, the multikinase inhibitor, such as axitinib, nintedanib, sunitinib, lenvatinib, regorafenib, ponatinib, pazopanib, riociguat, or a combination thereof, may be administered by focal injection into the lesions/fibroids or their surrounding or adjacent tissues. For example, the multikinase inhibitor may be administered intrauterine injections using needles, devices, catheters, etc. It may be intrauterine instillation or perfusion (soaking). Focal administration may have the advantage of reduced toxicity as compared to a more systemic administration. This method of administering the multikinase inhibitor may be helpful to reduce the size and numbers of or eliminate the lesions, to prevent the growth of lesions/uterine fibroids and/or intrauterine adhesions or destruction of the endometrial lining, and/or uterine scarring and bleeding.

Primary sclerosing cholangitis (PSC) is a chronic immune mediated liver disease characterized by inflammation and fibrosis of both intra- and extrahepatic bile ducts. It affects the biliary tree resulting in multiple strictures and eventual cirrhosis. Histologic findings include periductal fibrosis and periportal eosinophilic infiltrate. Proposed focal treatment for PSC may include intra- and peri-bile duct treatment, cholangioplasty (such as percutaneous or transhepatic).

Unless otherwise indicated, any reference to a compound such as a multi-kinase inhibitor, e.g. axitinib, nintedanib, sunitinib, lenvatinib, regorafenib, ponatinib, pazopanib, riociguat, includes pharmaceutically acceptable salts; prodrugs; alternate solid forms, such as polymorphs, solvates, hydrates, etc.; tautomers; or any other chemical species that may rapidly convert to a compound described herein under conditions in which the compounds are used as described herein.

In some embodiments, administering a multikinase inhibitor, such as axitinib, nintedanib, sunitinib, lenvatinib, regorafenib, ponatinib, pazopanib, or riociguat, is effective in reducing the volume or weight of the affected tissue by at least about 1%, at least about 2%, at least about 3%, at least about 4%, at least about 5%, at least about 6%, at least about 7%, at least about 8%, at least about 9%, at least about 10%, at least about 12%, at least about 15%, or at least about 20%.

In some embodiments, administering a multikinase inhibitor, such as axitinib, nintedanib, sunitinib, lenvatinib, regorafenib, ponatinib, pazopanib, or riociguat, is effective in reducing the hyperplasia score of the affected tissue by at least about 1%, at least about 5%, at least about 10%, at least about 15%, at least about 20%, at least about 25%, at least about 30%, at least about 35%, or at least about 40%.

In some embodiments, administering a multikinase inhibitor, such as axitinib, nintedanib, sunitinib, lenvatinib, regorafenib, ponatinib, pazopanib, or riociguat, is effective in reducing blood vessel area or volume of the affected tissue to less than 70%, less than 50%, less than 25%, less than 20%, less than 15%, or less than 10% of its original blood vessel area or volume.

The therapeutic activity of multikinase inhibitors may be correlated with their inhibition of certain growth factors and cytokines, such as VEGF, PDGF, and TGF beta. Furthermore, some multikinase inhibitors demonstrated an effect of reducing inflammation and CD4+ and CD8+ lymphocytes.

In some embodiments, administering a multikinase inhibitor, such as axitinib, nintedanib, sunitinib, lenvatinib, regorafenib, ponatinib, pazopanib, or riociguat, is effective in inhibiting the activity of a VEGF by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

In some embodiments, administering a multikinase inhibitor, such as axitinib, nintedanib, sunitinib, lenvatinib, regorafenib, ponatinib, pazopanib, or riociguat, is effective in inhibiting the activity of a PDGF by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

In some embodiments, administering a multikinase inhibitor, such as axitinib, nintedanib, sunitinib, lenvatinib, regorafenib, ponatinib, pazopanib, or riociguat, is effective in inhibiting the activity of a TGF beta, such as TGFb-1 mRNA expression, by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

In some embodiments, administering a multikinase inhibitor, such as axitinib, nintedanib, sunitinib, lenvatinib, regorafenib, ponatinib, pazopanib, or riociguat, is effective in reducing inflammation by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

In some embodiments, administering a multikinase inhibitor, such as axitinib, nintedanib, sunitinib, lenvatinib, regorafenib, ponatinib, pazopanib, or riociguat, is effective in reducing CD4+ lymphocytes by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

In some embodiments, administering a multikinase inhibitor, such as axitinib, nintedanib, sunitinib, lenvatinib, regorafenib, ponatinib, pazopanib, or riociguat, is effective in reducing CD8+ lymphocytes by at least about 1%, at least about 5%, at least about 10%, at least about 20%, at least about 30%, at least about 40%, at least about 50%, at least about 60%, at least about 70%, at least about 80%, at least about 90%, at least about 95%, at least about 98%, or at least about 99%.

Generally, the amount of the multikinase inhibitor administered will depend upon the size of the lesion or fibroid being treated. For example, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of the multikinase inhibitor may be administered per lesion.

These amounts in the immediately preceding paragraph may be administered as needed, or at an interval of about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1 month, about 2 months, about 3 months, about 4 months, about 5 months, about 6 months, about 7 months, about 8 months, about 9 months, about 10 months, about 11 months, or about 12 months.

The treatment in the immediately preceding paragraph may be continued for as long as needed, such as only once, or for at least about 2 weeks, at least about 3 weeks, at least about 4 weeks, at least about 5 weeks, at least about 2 months, at least about 3 months, at least about 6 months, at least about 9 months, at least about 12 months, at least about 2 years, at least about 3 years, at least about 4 years, at least about 5 years, at least about 10 years, or at least about 20 years.

For treatments where the multikinase inhibitor is axitinib, about 0.0001-100 mg, about 0.001-10 mg, 0.0005-0.002 mg, about 0.002-0.003 mg, about 0.003-0.004 mg, about 0.004-

0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of axitinib may be administered per lesion. The dose of axitinib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is nintedanib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of nintedanib may be administered per lesion. The dose of nintedanib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is sunitinib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of sunitinib may be administered per lesion. The dose of sunitinib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is lenvatinib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of lenvatinib may be administered per lesion. The dose of lenvatinib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is regorafenib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of regorafenib may be administered per lesion. The dose of regorafenib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is ponatinib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of ponatinib may be administered per lesion. The dose of ponatinib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is pazopanib, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of pazopanib may be administered per lesion. The dose of pazopanib referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

For treatments where the multikinase inhibitor is riociguat, about 0.0001-100 mg, about 0.001-10 mg, 0.0005-0.002 mg, about 0.002-0.003 mg, about 0.003-0.004 mg, about 0.004-0.005 mg, about 0.005-0.006 mg, about 0.006-0.007 mg, about 0.007-0.008 mg, about 0.008-0.009 mg, about 0.009-0.01 mg, about 0.01-0.011 mg, about 0.1-0.5 mg, about 0.5-1 mg, about 1-1.5 mg, about 1.5-2 mg, about 2-2.5 mg, about 2.5-3 mg, about 3-3.5 mg, about 3.5-4 mg, about 4-4.5 mg, about 4.5-5 mg, about 5-5.5 mg, about 5.5-6 mg, about 6-6.5 mg, about 6.5-7 mg, about 7-7.5 mg, about 7.5-8 mg, about 8-8.5 mg, about 8.5-9 mg, about 9-9.5 mg, about 9.5-10 mg, about 10-10.5 mg, about 10.5-11 mg, about 11-11.5 mg, about 11.5-12 mg, about 12-12.5 mg, about 12.5-13 mg, about 13-13.5 mg, about 13.5-14 mg, about 14-14.5 mg, about 14.5-15 mg, about 15-15.5 mg, about 15.5-16 mg, about 16-16.5 mg, about 16.5-17 mg, about 17-17.5 mg, about 17.5-18 mg, about 18-18.5 mg, about 18.5-19 mg, about 19-19.5 mg, about 19.5-20 mg, about 1-3 mg, about 3-5 mg, about 5-7 mg, about 7-9 mg, about 9-11 mg, about 11-13 mg, about 13-15 mg, about 15-17 mg, about 17-19 mg, about 19-21 mg, about 1-5 mg, about 5-10 mg, about 10-15 mg, or about 15-20 mg of riociguat may be administered per lesion. The dose of riociguat referred to above may be continued as needed, or may be administered about weekly, about twice a month, about monthly, about every other month, about semi-annually, or about yearly. Treatment may occur once, or may be continued for at least about 1 month, at least about 2 months, at least about 3 months, at least about 6 months, at least about 1 year, at least about 2 years, or at least about 5 years.

The preparation of pharmaceutical compositions described herein can be conducted in accordance with generally accepted procedures for the preparation of pharmaceutical preparations. See, for example, Remington's Pharmaceutical Sciences 18th Edition (1990), E. W. Martin ed., Mack Publishing Co., PA. Liquid forms for administration by injection, include aqueous solution, aqueous or oil suspensions, emulsions, microbeads, etc. Suitable excipients may include solvents and/or co-solvents; solubilizing, wetting, suspending, emulsifying or thickening agents; chelating agents; antioxidants and reducing agents; antimicrobial preservatives; buffers and/or pH. adjusting agents; bulking agents; protectants; tonicity adjustors; etc. The dosage form may be stored as a liquid or reconstituted for use.

Some embodiments will be illustrated with the following specific examples. One skilled in the art would appreciate that these examples are for illustration only and are not meant to limit the scope of the invention because other modifications and variations are possible based on the examples disclosed herein.

Example 1

Uterine fibroids are benign hyperplasia. Uterine fibroids and benign prostate hyperplasia are both manifested as benign tissue overgrowth. The former is dependent on the estrogen and progesterone, and the latter has been shown to be dependent on endogenous testosterone. These reproductive tract dysplasia are also linked by documented roles for growth factors such as VEGF and TGF beta in both diseases (Tal, R. and Segars, J. H., Hum. Reprod. Update, 20:

194-216, 2014; Walsh, K. et al., Prostate Cancer and Prostatic Dis., 5: 119-122, 2002; Soulitzis, N. et al., Int. J. Oncol., 29: 305-314, 2006).

Morphologically, benign prostate hyperplasia is characterized by the formation of a new architecture through the proliferation of the epithelium in pre-existing ducts. Given that stromal cells serve important paracrine regulatory functions in epithelial cell homeostasis, late stage changes in stromal-epithelial interactions could provide insight into uterine fibroids.

Wistar and Sprague-Dawley strains of rats are susceptible to developing benign prostatic hyperplasia after treatment with exogenous testosterone and can serve as a model of hyperplasia induced by endogenous hormones, i.e., BPH in males and uterine fibroids (UF) in females. A study was conducted to determine the effects of test compounds and vehicle on testosterone and phenylephrine induced benign prostate hyperplasia in rats. Male Wistar rats were induced with testosterone (2 mg/kg) plus phenylephrine (5 mg/kg) administered daily by subcutaneous injection on days 1 through 28. Vehicle or the multikinase test compounds, axitinib (1%), sorafenib (1%), pirfenidone (2.5%) and riociguat (1%), were administered by intra-prostate injection (0.2 mL) on days 15 and 29. Animals were euthanized on day 42. Body weights were determined. Prostate glands were harvested and weighed. The study design is as shown in Table 1 below.

TABLE 1

Study Design Outline.

| Group (Test Article) | Dose (mg/kg) | Route of Administration | Day(s) of Administration | Animal Numbers |
|---|---|---|---|---|
| 1 (vehicle) | 0 | Intra-prostate | 15, 29 | 6 |
| 2 (axitinib 1%) | 2 | Intra-prostate | 15, 29 | 8 |
| 3 (sorafenib 1%) | 2 | Intra-prostate | 15, 29 | 8 |
| 4 (pirfenidone 2.5%) | 5 | Intra-prostate | 15, 29 | 7 |
| 5 N/A | N/A | N/A | N/A | 5 |
| 6 N/A | N/A | N/A | N/A | 7 |
| 7 (riociguat 1%) | 2 | Intra-prostate | 15, 29 | 7 |

For Groups 1 through 4, Testosterone and Phenylephrine was injected on days 1-28. For Groups 6 and 7, Testosterone was injected on days 1-28.

Prostate weight/100 g body weight was determined for each treatment group (FIG. 1). Axitinib and riociguat treatment resulted in a reduction in the mean prostate weight, as compared to their vehicle-treated controls, i.e., groups 1 and 6, respectively. Sorafenib did not show a reduction in the mean prostate weight, as compared to the vehicle-treated control group (group 1), indicating that not all multikinase inhibitors would work. Rather, only multikinase inhibitors with a certain inhibitory spectrum would work.

At necropsy, the dorsolateral and ventral lobes of the prostate were separated and cut into halves. The left halves were fixed in 10% neutral buffered formalin, sectioned, and stained with Hematoxylin and Eosin (H&E). Glandular hyperplasia was recognized as an increase in epithelial cells within normal appearing gland profiles, reflected by stratification of epithelial cells and increased presence of epithelial tufting and papillary projections (FIG. 2). Stromal changes were examined microscopically. These changes included inflammation and tissue fibroplasia. Each section was given a severity score ranging from 0 (not present) through 5 (severe).

FIG. 2 shows effects of test agents on testosterone and phenylephrine induced fibroplasia in rats. Representative images from dorsolateral prostate at 100× magnification are shown. Panel (1) shows the image of Group 5 (vehicle) rat showing a normal (score=0) glandular profile. Panel (2) shows Group 1 (testosterone and phenylephrine, TE+PE, induced and vehicle-treated) rat with slight (score=2) epithelial hyperplasia. Panel (3) shows Group 2 (TE+PE induced and axitinib 1%-treated) rat with minimal (score=1) epithelial hyperplasia. Panel (4) shows Group 3 (TE+PE induced and sorafenib 1%-treated) rat with slight (score=2) epithelial hyperplasia. Panel (5) shows Group 4 (TE+PE induced and pirfenidone 2.5%-treated) rat with minimal (score=1) epithelial hyperplasia. Panel (6) shows Group 6 (TE-induced) rat with slight (score=2) epithelial hyperplasia. Panel (7) shows Group 7 (TE induced and riociguat 1%-treated) rat with minimal (score=1) epithelial hyperplasia.

As shown in FIG. 3, axitinib, pirfenidone, and riociguat demonstrated a decrease in hyperplasia scores, as compared to the vehicle treatment. In contrast, sorafenib treatment did not lead to reduction in hyperplasia, as compared to the vehicle group.

Inhibition of hyperplasia induced by testosterone and/or epinephrine by axitinib, pirfenidone, and riociguat indicates that these compounds would be effective in the treatment of benign tissue overgrowth and/or disorders resulting from cell proliferation and fibrosis in the digestive and reproductive systems. This study shows that not all multikinase inhibitors with ant-VEGFR and anti-PDGFR activity will be effective inhibitors of hormonal induced hyperplasia.

Example 2

Concentration of Axitinib and Sorafenib after Intraprostate Injection in the Rat In this study, intraprostate injections of axitinib and sorafenib were administered on Days 15 and 29. Animals were euthanized on Day 42 and prostate tissue samples were collected for analysis. Tissue samples were prepared using a Bead Ruptor homogenizer, followed by extraction with acetonitrile and high-speed centrifugation. An LC-MS/MS method for measurement of axitinib and sorafenib was developed with the use of an internal standard of axitinib-d3.

On day 42, the mean concentration of axitinib in the prostate was 718 mg/gm, and that of sorafenib in the prostate was 892 mg/gm.

Both of these tissue concentrations are higher than required for inhibition of VEGFR and PDGFR activity. Results from this study indicate that any differences in pharmacological activity in the prostate gland between axitinib and sorafenib are not due to differences in their pharmacokinetic profiles.

Example 3

This study was conducted to determine the effects of multikinase inhibitors and vehicle on testosterone and phenylephrine induced benign prostate hyperplasia in rats. Male Wistar rats were induced with testosterone (2 mg/kg) plus phenylephrine (5 mg/kg) administered daily by subcutaneous injection on days 5 through 32. Vehicle or test compounds (all 1% w/v), nintedanib, sunitinib or lenvatinib and doxazosin mesylate, were administered by intra-prostate injection (0.4 ml) in dorsolateral and ventral lobes on days 1 and 18. Animals were euthanized on day 32. The study design is as shown in Table 2 below.

At necropsy, the ventral and dorsolateral lobes of the prostate were separated and then cut into halves. The left halves were fixed in 10% neutral buffered formalin, sectioned, and stained with Hematoxylin and Eosin (H&E). Histological changes in these sections were scored. Epithelial hyperplasia was recognized as an increase in epithelial cells within normal-appearing gland profiles, primarily reflected by stratification of epithelial cells and increased presence of epithelial tufting and papillary projections. A severity grade of 0 (not present) through 5 (severe) was assigned to each sample. Representative images are presented in FIGS. 4 and 5. The mean scores (+/−SD) are shown in FIGS. 6 and 7.

TABLE 2

Study Design Outline.

| Group* (Test Article) | Dose (mg/kg) | Route of Administration | Day(s) of Administration | Animal Numbers |
|---|---|---|---|---|
| 1 (Vehicle) | 0 | Intra-prostate | 1, 18 | 6 |
| 2 (nintedanib 1%) | 4 | Intra-prostate | 1, 18 | 6 |
| 3 (sunitinib 1%) | 4 | Intra-prostate | 1, 18 | 6 |
| 4 (lenvatinib 1%) | 4 | Intra-prostate | 1, 18 | 6 |
| 5 (doxazosin 0.5%) | 2 | Intra-prostate | 1, 18 | 6 |
| 6 (Vehicle) | 0 | Intra-prostate | 1, 18 | 6 |

*All animals received TE and PE, except Group 1.

Figure 4:
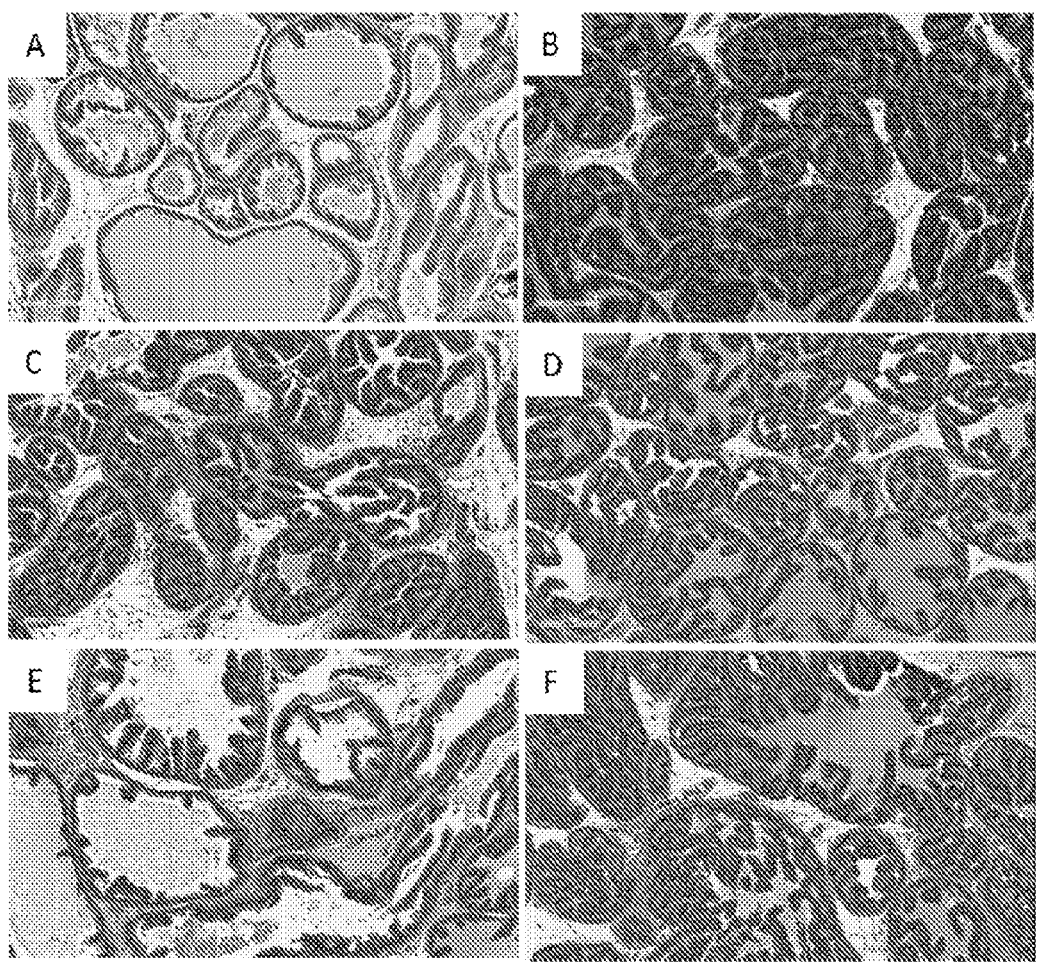
FIG. 4 shows representative images of glandular hyperplasia in dorsolateral prostate at 100× magnification.

FIG. 4 shows the effects of test agents on glandular hyperplasia in the dorsolateral prostate. Panel (A) shows vehicle-treated tissue showing normal (score=0) glandular profile. Panel (B) shows TE+PE induced and vehicle-treated with marked (score=4) epithelial hyperplasia. Panel (C) shows TE+PE induced and nintedanib-treated) with moderate (score=3) epithelial hyperplasia. Panel (D) shows TE+PE induced and sunitinib-treated) with moderate (score=3) epithelial hyperplasia. Panel (E) shows TE+PE induced and lenvatinib-treated) with slight (score=2) epithelial hyperplasia. Panel (F) shows TE+PE induced and doxazosin -treated) with moderate (score=3) epithelial hyperplasia.

Figure 5:
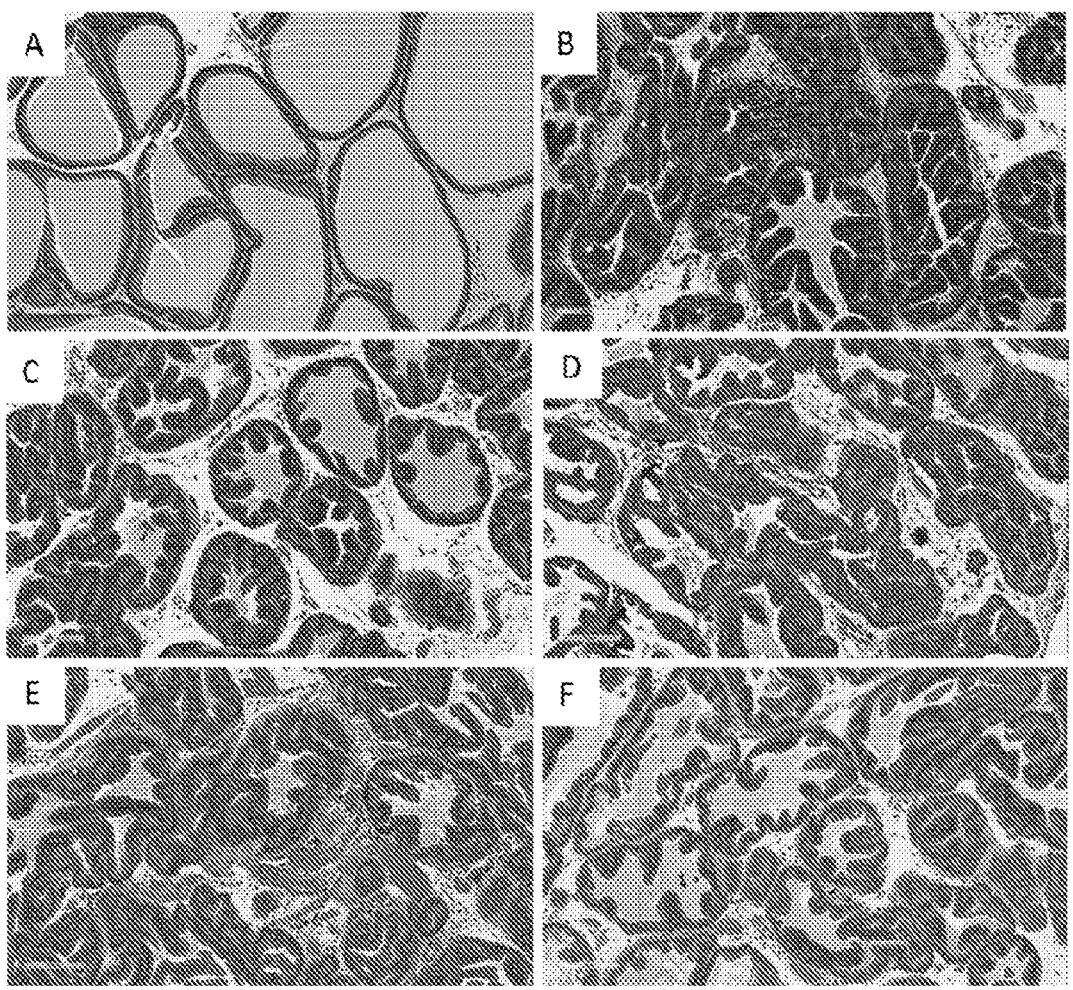
FIG. 5 shows representative images of glandular hyperplasia in ventral prostate. Representative images from ventral prostate are shown at 100× magnification.

FIG. 5 shows the effects of test agents on glandular hyperplasia in the ventral prostate. Panel (A) shows vehicle-treated showing normal (score=0) glandular profile. Panel (B) shows TE+PE induced and vehicle-treated with marked (score=4) epithelial hyperplasia. Panel (C) shows TE+PE induced and nintedanib-treated) with moderate (score=3) epithelial hyperplasia. Panel (D) shows TE+PE induced and sunitinib-treated) with moderate (score=3) epithelial hyperplasia. Panel (E) shows TE+PE induced and lenvatinib -treated) with slight (score=3) epithelial hyperplasia. Panel (F) shows TE+PE induced and doxazosin-treated) with moderate (score=3) epithelial hyperplasia.

Mean scores for the effects of nintedanib, sunitinib, lenvatinib and doxazosin on glandular hyperplasia in the dorsolateral and ventral prostate are given in FIG. 6 and FIG. 7.

This study shows that nintedanib and lenvatinib to be effective inhibitors of cellular proliferation in a testosterone/phenylephrine induced benign prostate hyperplasia model in rat.

Inhibition of benign prostate hyperplasia in the two studies described above by nintedanib, sunitinib, lenvatinib and doxazosin indicates that these compounds would be effective in the treatment of benign tissue overgrowth and/or disorders resulting from cell proliferation and fibrosis in the digestive and reproductive systems.

Example 4

Fibroplasia is, generally, a late phase reactive and/or reparative response in tissues associated with disease, trauma, genetic disorders, or infection. There is a strong overlap in the pathophysiology regardless of the organ or tissue involved, so that observations made in ocular tissue, for example, could be relevant to reproductive and/or digestive tract diseases and/or disorders.

A study was conducted to determine the potential beneficial effects of topical administration of test compounds and vehicle in a suture induced ocular fibrosis model in rabbits. Sutures were placed intrastromally, under a microscope, in the cornea of rabbits. In each eye, one 9.0 silk suture was placed, in a vertical position, temporal to the center of the cornea and a second suture was placed nasal to the corneal center. Each suture had two stromal incursions approximately 2 mm from the limbus. Test compounds having a certain spectrum of multikinase inhibition activities or vehicle were topically instilled (35 µL/eye) in the eyes three times daily for 10 days following the day of surgery. The treatment groups include vehicle, axitinib (0.3%), nintedanib (0.3%), pirfenidone (1%), riociguat (0.3%), sorafenib (0.3%) and lenvatinib (0.3%). Six left eyes were used per treatment group.

During the in-life phase, gross ocular observations of very slight to moderate conjunctival congestion and swelling were similar among groups, including the vehicle control. The animals were sacrificed on Day 11 and eyes enucleated and dissected for histopathological evaluation.

The results show that axitinib, lenvatinib, nintedanib and sorafenib were efficacious in reducing the areas of neovascularization on the corneal surface (FIG. 8). In addition, axitinib, nintedanib and lenvatinib significantly reduced fibroplasia and/or collagen density as evidenced by histological staining. In contrast, sorafenib had little or no effect on fibroplasia or collagen formation. In addition, axitinib, nintedanib and lenvatinib significantly reduced alpha SMA staining as determined by immunohistochemical analysis, while sorafenib had no effect on alpha SMA relative to vehicle treatment (FIG. 9).

Study results show histological reduction in neovascularization, fibroplasia, collagen-related materials, and SMA by axitinib, nintedanib, and lenvatinib. Results from this study also show that not all multikinase inhibitors will be effective in treating fibrotic tissue responses.

Example 5

Fibrosis is a late phase reactive and/or reparative response in tissues associated with disease, trauma, genetic disorders, or infection. There is a strong overlap in the pathophysiology of fibrosis regardless of the organ or tissue involved, so that observations made in dermal wounds, for example, could be relevant to reproductive and/or digestive tract fibrosis. This would include examination of the role of growth factors such as VEGF, PDGF, FGF and/or TGF beta. In particular, TGF beta has been shown to be important in cutaneous wound healing and scarring and is expected to be a significant contributor to digestive and reproductive tract fibrotic responses.

Test compounds were examined in full-thickness dermal wounds in rabbits. Seven male New Zealand White rabbits, ranging in body weight from 3.03 to 3.40 kg were used in this study. Four wounds were placed on the ventral surface of both ears using an 8 mm skin punch biopsy. Axitinib (1.0%), nintedanib (1.0%), lenvatinib (1.0%), sorafenib (1.0%) and sunitinib (1.0%) were administered by intradermal or intralesional injection on days 15 and 29 following surgery. Animals were euthanized on Day 42 and trauma sites were harvested and divided in half. One half was preserved in formalin for histological examination and the other half frozen for TGF beta analysis.

Tissue H&E staining was evaluated semi-quantitatively for inflammation and neovascularization. Tissue fibrosis and collagen organization were evaluated by Mason's trichrome staining. Scores for four intradermal sites receiving test articles were averaged for each rabbit. Most scar tissues were composed of neovascularization, fibroblast hyperplasia, collagen disorganization and re-epithelialization.

Axitinib (Table 3) had less neovascularization than untreated wounds. The average total score of the test wounds was 1.4 lower than the untreated wounds.

TABLE 3

Histopathology Findings of Rabbit Ear Wound Treated with Intradermal Dosing of 1% Axitinib

|  | Neovascularization | Fibrosis/Collagen | Reepithelialization | Total Score |
|---|---|---|---|---|
| Treated Mean | 1 | 3.3 | 0.3 | 4.6 |
| Untreated Control | 3 | 3 | 0 | 6 |

Nintedanib (Table 4) had much less neovascularization and about the same fibrosis as untreated wounds. The average total score of the test wounds was 1.5 lower than untreated wounds. Overall, the test sites have less scar formation compared with the control sites.

TABLE 4

Histopathology Findings of Rabbit Ear Wound Treated with Intradermal Dosing of 1% Nintedanib

|  | Neovascularization | Fibrosis/Collagen | Reepithelialization | Total Score |
|---|---|---|---|---|
| Treated Mean | 1 | 3 | 0.5 | 4.5 |
| Untreated Control | 3 | 3 | 0 | 6 |

Sorafenib (Table 5) had slightly increased neovascularization and similar, or increased fibrosis compared to control sites. Overall, the test article does not appear to have reduced scar formation compared to untreated wound sites.

TABLE 5

Histopathology Findings of Rabbit Ear Wound Treated with Intradermal Dosing of 1% Sorafenib.

|  | Neovascularization | Fibrosis/Collagen | Reepithelialization | Total Score |
|---|---|---|---|---|
| Treated Mean | 3 | 2.5 | 0.3 | 5.8 |
| Untreated Control | 2 | 2 | 0 | 4 |

Sunitinib (Table 6) had slightly increased neovascularization and increased fibrosis compared to untreated control sites. Overall, the test article does not appear to have reduced scar formation compared to untreated wound sites.

TABLE 6

Histopathology Findings of Rabbit Ear Wound Treated with Intradermal Dosing of 1% Sunitinib.

|  | Neovascularization | Fibrosis/Collagen | Reepithelialization | Total Score |
|---|---|---|---|---|
| Treated Mean | 4 | 3.7 | 0 | 7.7 |
| Untreated Control | 2 | 2 | 0 | 4 |

Lenvatinib (Table 7) appeared to have to have decreased fibrosis compared to control wound sites. The total score was 0.5 lower than the control wound.

TABLE 7

Histopathology Findings of Rabbit Ear Wound Treated with Intradermal Dosing of 1% Lenvatinib.

|  | Neovascularization | Fibrosis/Collagen | Reepithelialization | Total Score |
|---|---|---|---|---|
| Treated Mean | 2 | 2.5 | 0 | 4.5 |
| Vehicle Control | 2 | 3 | 0 | 5 |

The histopathology data for axitinib, nintedanib and lenvatinib treated trauma sites show decreased angiogenesis and fibrosis. In contrast, samples from sorafenib or sunitinib treated sites do not show any reduction in angiogenesis and fibrosis.

TGF beta mRNA expression in treated trauma samples was compared to expression in untreated samples. In general, TGF beta expression in treated samples was lower relative to untreated trauma samples.

The mean folds of TGF beta mRNA expression in axitinib, nintedanib and lenvatinib treated samples are lower than the expression level in untreated trauma samples. In contrast, samples from animals treated with other multikinase inhibitors, such as sorafenib or sunitinib, do not show mean TGF beta expression levels significantly different from the untreated trauma samples (FIG. 10).

These data support the fact that axitinib, nintedanib and lenvatinib possess a certain spectrum of multikinase inhibitory activities necessary to treat disease states, disorders and surgical procedures associated with fibrosis. The certain spectrum of multikinase inhibition may be involved in the signaling pathway of TGF beta.

Example 6

Inhibition of fibrosis and collagen deposition seems to be correlated with a multikinase's ability to blunt an increase in TGF beta mRNA expression. Since tissue levels of TGF beta reflect both stored and processed content of the growth factor, as well as new protein synthesis, we have measured TGF beta protein levels in a second dermal wound response using minipigs.

Full-thickness linear incision wounds were created in Gottingen minipigs on Day 1. 10 wounds approximately 3 cm in length and spaced at least 5 cm apart were created on the dorsal surface of the animals, perpendicular to the spine. Test agents included nintedanib (2%), lenvatinib (2%), sorafenib (1%), axitinib (2%) and vehicle control. Test agents were administered by intradermal injection immediately after wound creation. The dose of nintedanib, lenvatinib, sorafenib, or axitinib was 16 mg per wound site. Three minipigs were dosed in a similar manner. One minipig was sacrificed on Day 4, one on Day 7, and one on Day 9.

At the time of sacrifice, two dermal punch biopsies (4 mm) from each side of the wound sites were collected. Two biopsies were flash frozen in liquid nitrogen and stored at −80° C. prior to processing by protein extraction and ELISA (enzyme-linked immunosorbent assay) analysis. TGF beta protein levels were measured on Days 4, 7 and 9.

FIG. 11 shows that axitinib, nintedanib and lenvatinib exhibited a time-dependent inhibition of TGF beta 1 protein levels in the pig linear incision wound model. Sorafenib was much less effective in this model of dermal wound healing.

Example 7

Human cathelicidin LL-37 and its mouse ortholog have been associated with mucosal immunity at several sites in respiratory epithelium, in vitamin D deficiency in tuberculosis, in host defense against bacterial and viral infections in vitro, and in mouse models. In the GI tract, LL-37 levels are elevated in ulcerative colitis and in Helicobacter pylori infection of stomach. The colonic epithelium expresses the human cathelicidin LL-37 with levels higher in biopsies of inflamed colon. Individuals with rosacea not only express high levels of cathelicidin, but also produce forms of cathelicidin peptides which promote leukocyte chemotaxis, angiogenesis, and expression of extracellular matrix components. It has been shown that injection of these peptides into the skin of mice results in skin inflammation resembling pathological changes seen in rosacea patients. A cathelicidin derived peptide LL-37 has been used to induce rosacea-like responses in mice.

In our study, mice were injected subcutaneously with 40 μL of LL-37 (3.3 mg/mL) to induce inflammatory reactions. Immediately following the LL-37 injection, axitinib, nintedanib, and lenvatinib were individually administered as a single intradermal injection (1.6 mg). LL-37 injection was repeated every 12 hours for a total of 4 injections. Endotoxin-free water and dexamethasone (3 mg/kg by intraperitoneal injection, twice), respectively, were used as negative and positive control groups.

At 48 hours after the initial LL-37 injection, the dorsal skin was photographed, and the severity of skin lesions were scored for redness and measured for areas of involvement.

At 48 hours after the initial LL-37 injection, the dorsal skin was photographed, and the severity of skin lesions were scored for redness and measured for areas of involvement.

As shown in FIG. 12, among all treatment groups, lenvatinib (AIV007) showed the lowest TGFb-1 mRNA expression. The TGFb1 mRNA expression in mice induced with LL37 and treated with lenvatinib was 79% of that challenged with LL37 alone (i.e., without treatment).

The tissue samples were analyzed for inflammation characteristics. Histopathology endpoints included inflammation, and CD4+ and CD8+ T-lymphocyte immunostaining. For inflammation scores, tissues were examined histologically and scored for inflammatory cell infiltrate. As shown in FIG. 13, axitinib, nintedanib, and lenvatinib showed prominent reductions in the scores of inflammation. These results indicate that the multi-kinase inhibitors listed herein will be effective therapeutic agents for preventing or treating diseases that are caused by or associated with inflammation.

As shown in FIG. 14, multi-kinase inhibitors oaxitinib, nintedanib, and levatinib, are also effective in the reduction of CD4+ lymphocyte scores in the mice model of inflammation induced by intradermal LL37 injections. The reductions range from about 30% to about 40%.

Similarly, as shown in FIG. 15, multi-kinase inhibitors axitinib, nintedanib, and levatinib, are also effective in the reduction of CD8+ lymphocyte scores in the mice model of inflammation induced by intradermal LL37 injections. The reductions range from about 40% to about 55%.

In summary, some of the compounds listed herein demonstrated inhibitory effects in LL37-induced inflammation. In addition, these compounds also regulate TGF beta mRNA expression. These results support the notion that these compounds possess an inhibitory profile necessary for the prevention and treatment of diseases characterized by inflammation, such as uterine fibroids, uterine fibroma, intramural fibroids, subserosal fibroids, submucosal fibroids, pedunculated fibroids, uterine leiomyomas, uterine myomas, adenomyosis, uterine fibromyoma, uterine fibroleiomyoma, cervical fibroids, uterine synechiae, Asherman's syndrome, biliary duct fibrosis, biliary duct sclerosis, primary biliary cirrhosis, and primary sclerosing cholangitis, or a combination thereof.

These data are consistent with the previous studies described above. Certain multikinase inhibitors, including axitinib, nintedanib and lenvatinib, are shown to be effective regulators of cell proliferation and fibrosis. Further, their activities are correlated with their inhibition of certain growth factors, such as TGF beta.

Unless otherwise indicated, all numbers expressing quantities or properties such as dose amount, hyperplasia score, and etc. used in herein are to be understood as being modified in all instances by the term "about." Each numerical parameter should at least be construed in light of the number of reported significant digits and by applying ordinary rounding techniques. Accordingly, unless indicated to the contrary, the numerical parameters may be modified according to the desired properties sought to be achieved, and should, therefore, be considered as part of the disclosure. At the very least, the examples shown herein are for illustration only, not as an attempt to limit the scope of the disclosure.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illustrate embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the embodiments. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating fibrosis associated with a reproductive tract or digestive tract disease or disorder, comprising: administering an effective amount of a multikinase inhibitor to an animal or a human being in need thereof, wherein the multikinase inhibitor is axitinib, sunitinib, lenvatinib, regorafenib, ponatinib, riociguat, a salt of any of these multikinase inhibitors, or a combination thereof, and wherein the reproductive tract or digestive tract disease or disorder comprises uterine fibroids, uterine fibroma, intramural fibroids, subserosal fibroids, submucosal fibroids, pedunculated fibroids, uterine leiomyomas, uterine myomas, adenomyosis, uterine fibromyoma, uterine fibroleiomyoma, cervical fibroids, uterine synechiae, Asherman's syndrome, biliary duct fibrosis, biliary duct sclerosis, primary biliary cirrhosis, primary sclerosing cholangitis, benign prostatic hyperplasia, or a combination thereof.

2. The method of claim 1, wherein the multikinase inhibitor is axitinib or a salt thereof.

3. The method of claim 1, wherein the multikinase inhibitor is lenvatinib or a salt thereof.

4. The method of claim 1, wherein the multikinase inhibitor is regorafenib or a salt thereof.

5. The method of claim 1, wherein the multikinase inhibitor is ponatinib or a salt thereof.

6. The method of claim 1, wherein the multikinase inhibitor is riociguat or a salt thereof.

7. The method of claim 1, wherein the multikinase inhibitor is administered to the human being.

8. The method of claim 1, wherein the fibrosis is associated with the reproductive tract disease or disorder.

9. The method of claim 1, wherein the fibrosis is associated with the digestive tract disease or disorder.

10. The method of claim 1, wherein the reproductive tract or digestive tract disease or disorder is associated with intra uterine surgery.

11. The method of claim 1, wherein the reproductive tract or digestive tract disease or disorder comprises intrauterine adhesions.

12. The method of claim 1, wherein the reproductive tract or digestive tract disease or disorder comprises intrauterine synachiae.

13. The method of claim 1, wherein administering the multikinase inhibitor occurs by intra-lesional, peri-lesional, intra-ductal, peri-ductal, trans-dermal, intra-muscular, intra-uterine, intra-prostate, intra-vascular administration, or a combination thereof.

* * * * *